(12) United States Patent
Lin

(10) Patent No.: US 8,500,662 B2
(45) Date of Patent: Aug. 6, 2013

(54) POWER DEVICE FOR VISUAL CARE

(76) Inventor: Yuan Tsang Lin, Taichung (TW)

( * ) Notice: Subject to any disclaimer, the term of this patent is extended or adjusted under 35 U.S.C. 154(b) by 313 days.

(21) Appl. No.: 13/030,215

(22) Filed: Feb. 18, 2011

(65) Prior Publication Data
US 2011/0306906 A1 Dec. 15, 2011

(30) Foreign Application Priority Data

Jun. 14, 2010 (TW) .................................. 99211348 U

(51) Int. Cl.
*A61H 9/00* (2006.01)
*A61H 5/00* (2006.01)

(52) U.S. Cl.
USPC .................................... 601/9; 601/13; 601/37

(58) Field of Classification Search
USPC .................. 601/6–7, 9–10, 13, 23, 37, 46, 49, 601/55, 61, 69, 75, 84, 96–97, 105, 107–108, 601/148; 91/218; 92/13, 15
See application file for complete search history.

(56) References Cited

U.S. PATENT DOCUMENTS

| | | | | | |
|---|---|---|---|---|---|
| 4,387,707 | A | * | 6/1983 | Polikoff | 601/37 |
| 4,428,368 | A | * | 1/1984 | Torii | 601/9 |
| 6,283,929 | B1 | * | 9/2001 | Mjehovic | 601/136 |
| 2003/0032901 | A1 | * | 2/2003 | Webb | 601/49 |
| 2006/0206041 | A1 | * | 9/2006 | Liu | 601/13 |

\* cited by examiner

*Primary Examiner* — Justine Yu
*Assistant Examiner* — Timothy Stanis
(74) *Attorney, Agent, or Firm* — Ming Chow; Sinorica, LLC

(57) ABSTRACT

A power device for visual care includes a circuit control fixed with a pneumatic cylinder. The circuit control panel includes a homing sensor, a positive air pressure micro switch and a negative air pressure micro switch respectively correspond to the homing position, the utmost positive air pressure position and the utmost negative air pressure position of a piston unit. The circuit control panel further includes a guide member with an inductive part. Accordingly, when the power unit is activated, a power screw drives the piston unit to bring the inductive part of the guide member to the homing sensor for return-to-zero setting, and to bring it to touch the positive air pressure micro switch and the negative air pressure micro switch so as to provide proper positive air pressure and negative air pressure for visual care.

2 Claims, 7 Drawing Sheets

POWER DEVICE FOR VISUAL CARE

BACKGROUND OF THE INVENTION

1. Field of the Invention

The present invention relates to a power device for visual care, and more particularly, to a power device having a homing sensor, a positive air pressure micro switch and a negative air pressure micro switch so as to provide proper air pressure.

2. Description of the Prior Art

A conventional air pressure assembly (10) incorporated with an air pipe (11) generates positive air pressure and negative air pressure to an eyeshade (not shown in the drawing) for visual care, which provides a pressure or suction effect for correcting vision or visual care.

The conventional air pressure assembly (10) comprises a motor (12) with a spindle (13) to drive a power screw (14). A screw seat (15) is screwed to the power screw (14) and coupled with a piston (16). A pneumatic cylinder (17) is fitted on the piston (16) and the screw seat (15). The pneumatic cylinder (17) has guide grooves (171, 172) corresponding to bearings (151, 152) of the screw seat (15) to ensure that the piston (16) slides thereon without rotation. When the motor (12) drives the spindle (13) and the power screw (14) to turn, the screw seat (15) and the piston (16) will be moved to reciprocate linearly, such that the piston (16) will generate positive/negative air pressure or suction which is sent to the eyeshade through the air pipe (11) for visual care.

However, the conventional air pressure assembly (10) has the following shortages. The conventional air pressure assembly (10) doesn't check position and return-to-zero. After a period of time, the positive/negative air pressure generated by the conventional air pressure assembly (10) may be too much or not enough. This will influence the effect of the visual care. Accordingly, the inventor of the present invention has devoted himself based on his many years of practical experiences to solve this problem.

SUMMARY OF THE INVENTION

According to the present invention, there is provided a power device for visual care. The power device comprises a circuit control panel. The circuit control panel is fixed to one side having a guide slot of a pneumatic cylinder. The circuit control panel has a notch corresponding in position to the guide slot. The circuit control panel comprises a homing sensor, a positive air pressure micro switch and a negative air pressure micro switch which are located close to the notch and respectively correspond to a homing position, an utmost positive air pressure position and an utmost negative air pressure position of the piston unit. The circuit control panel further includes a guide member having an inductive part which has a bent section facing the homing sensor. Accordingly, when the power unit is activated, the power screw drives the piston unit to bring the inductive part of the guide member to the homing sensor for return-to-zero setting and to bring the guide member to touch the positive air pressure micro switch and the negative air pressure micro switch and return to the homing sensor so as to provide proper positive air pressure and negative air pressure for visual care.

The power unit of the present invention is activated to turn the power screw and the power screw drives the piston unit to bring the inductive part of the guide member to the homing sensor for return-to-zero setting and to bring the guide member to touch the positive air pressure micro switch and the negative air pressure micro switch and return to the homing sensor to provide proper positive air pressure and negative air pressure for visual care.

DETAILED DESCRIPTION OF THE PREFERRED EMBODIMENTS

Figure 1:
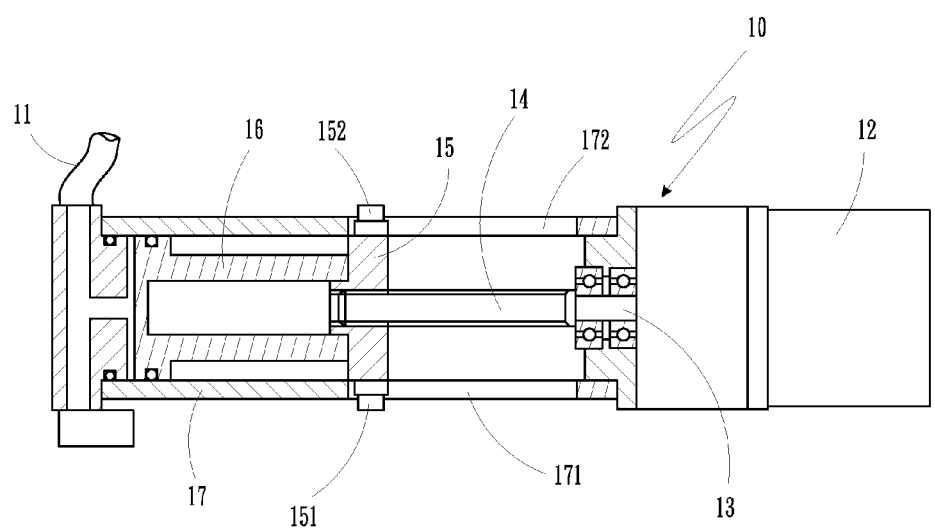
FIG. 1 is a cross-sectional view of a conventional air pressure assembly for visual care.
Figure 2:
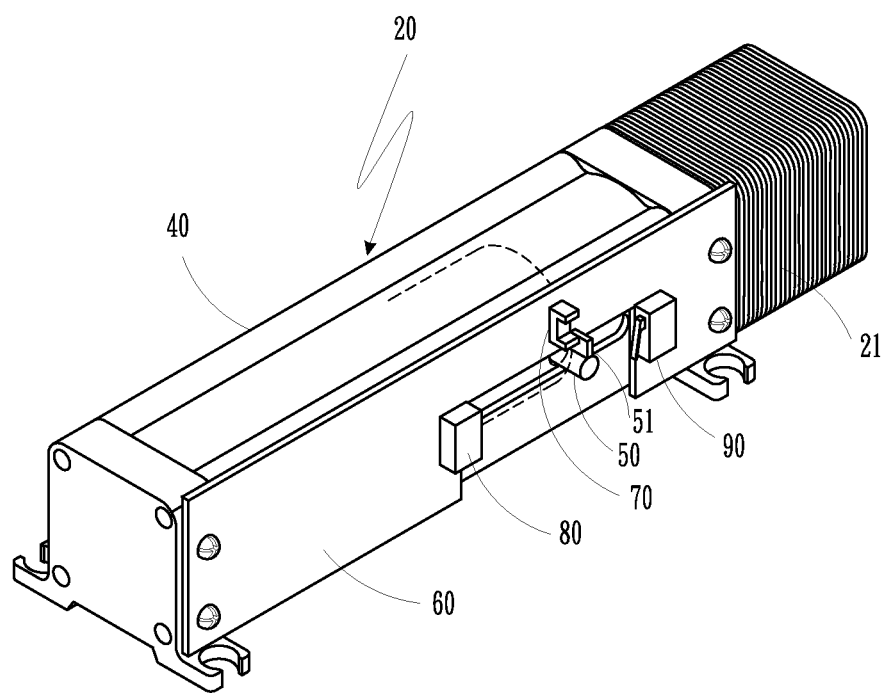
FIG. 2 is a perspective view according to a preferred embodiment of the present invention.
Figure 3:
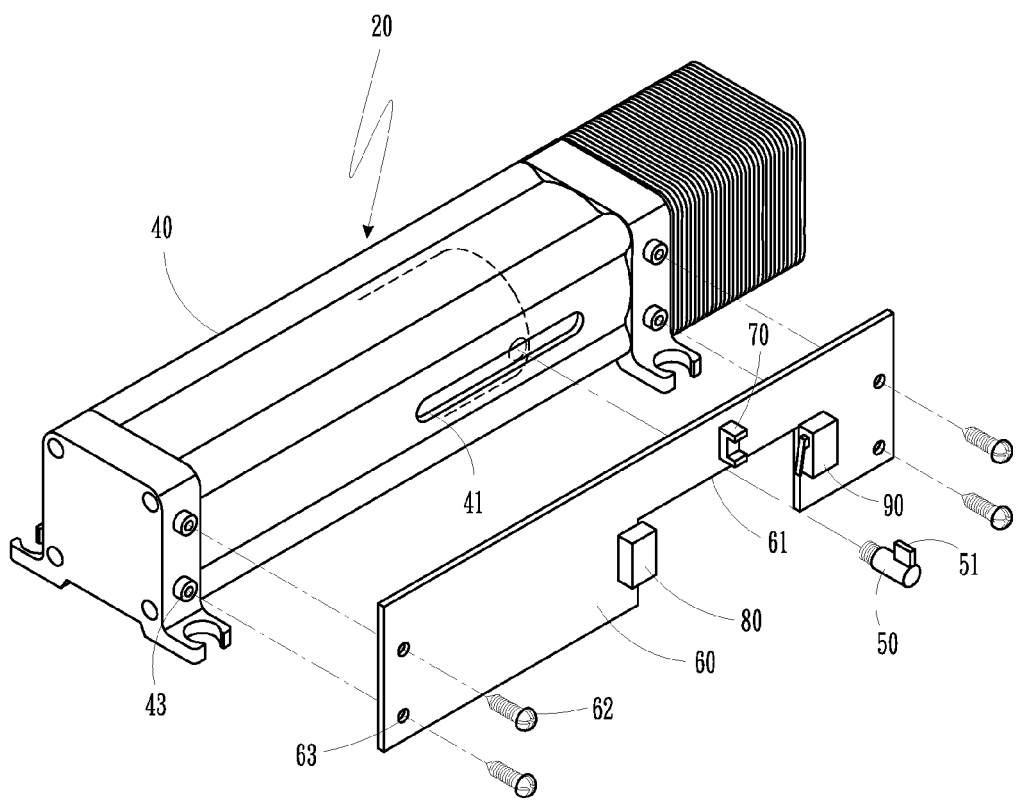
FIG. 3 is an exploded view according to the preferred embodiment of the present invention.
Figure 4:
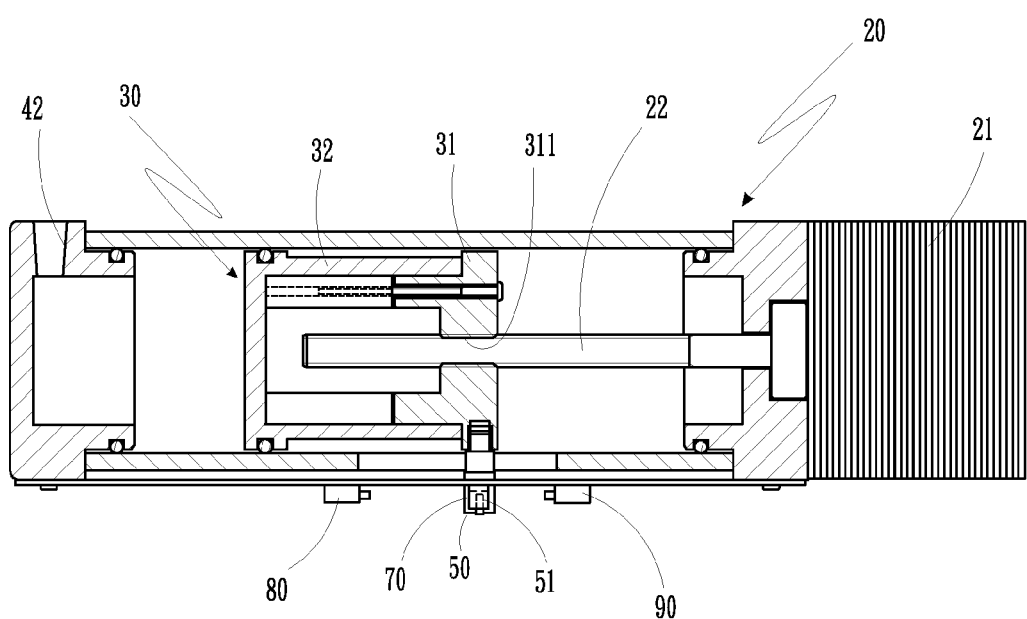
FIG. 4 is a cross-sectional view according to the preferred embodiment of the present invention.

Embodiments of the present invention will now be described, by way of example only, with reference to the accompanying drawings.

As shown in FIG. 2 to FIG. 5, a power device for visual care according to a preferred embodiment of the present invention comprises a power unit (20), a piston unit (30), a pneumatic cylinder (40), a guide member (50), and a circuit control panel (60). The power unit (20) comprises a motor (21) and a power screw (22) driven by the motor (21). The piston unit (30) comprises a screw seat (31) and a piston (32). The screw seat (31) has a threaded hole (311) for insertion of the power screw (22). The pneumatic cylinder (40) is fitted on the piston (32) and the screw seat (31) of the piston unit (30). The pneumatic cylinder (40) has a guide slot (41) disposed on one side thereof. The guide member (50) is inserted in the guide slot (41) and fixed to the screw seat (31). The circuit control panel (60) is fixed to the side having the guide slot (41) of the pneumatic cylinder (40). The circuit control panel (60) has a notch (61) corresponding in position to the guide slot (41). The circuit control panel (60) comprises a homing sensor (70), a positive air pressure micro switch (80) and a negative air pressure micro switch (90) which are located close to the notch (61) and respectively correspond to the homing position, the utmost positive air pressure position and the utmost negative air pressure position of the piston unit (30). The guide member (50) comprises an inductive part (51) which has a bent section facing the homing sensor (70). Accordingly, when the power unit (20) is activated, the power screw (22) will drive the piston unit (30) to bring the inductive part (51) of the guide member (50) to the homing sensor (70) for return-to-zero setting and to bring the guide member (50) to touch the positive air pressure micro switch (80) and the negative air pressure micro switch (90) and return to the homing sensor (70) so as to provide proper positive air pressure and negative air pressure for visual care.

The circuit control panel (60) is fixed to the side having the guide slot (41) of the pneumatic cylinder (40) by a plurality of screws (62) which are inserted in holes (63) of the circuit control panel (60) and fixed to threaded holes (43) of the pneumatic cylinder (40).

The guide member (50) is fixed to the screw seat (31) of the piston unit (30) and exposed out of the guide slot (41) of the pneumatic cylinder (40). The guide slot (41) is adapted to limit movement of the piston unit (30) and to prevent the piston unit (30) from rotation. When the motor (21) drives the power screw (22) to turn, the screw seat (31) and the piston (32) will be linearly moved, such that the piston (32) is reciprocated to generate positive/negative air pressure or suction which is sent to an eyeshade through an outlet (42) for visual care.

Figure 5:
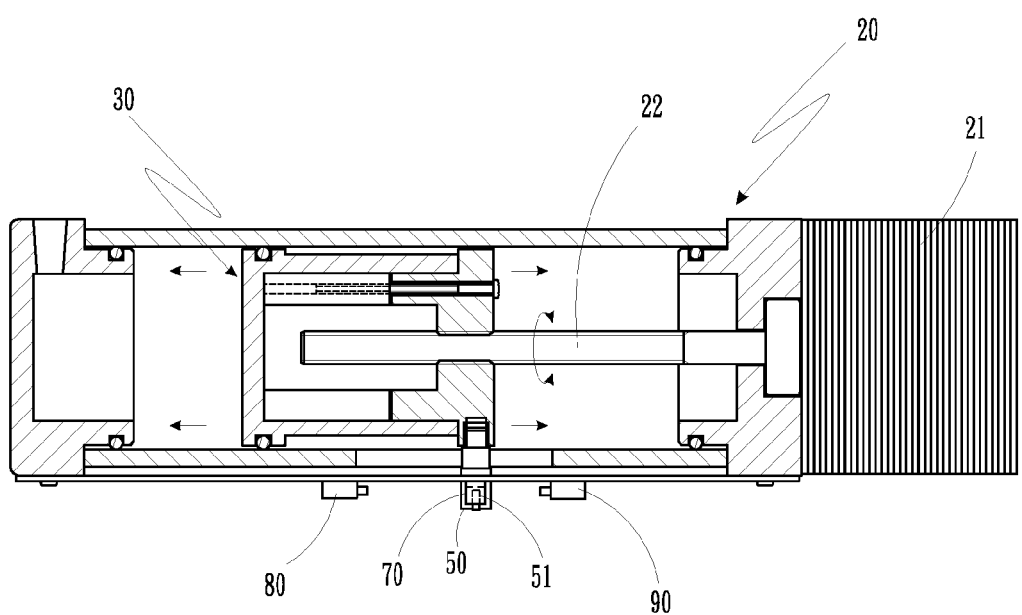
FIG. 5 is a top sectional view to show operation of return-to-zero according to the preferred embodiment.

Referring to FIG. 5, when the power unit (20) is activated, the motor (21) will drive the power screw (22) to turn and the power screw (22) will drive the piston unit (30) to bring the inductive part (51) of the guide member (50) to the homing sensor (70) for return-to-zero setting and to bring the guide member (50) to touch the positive air pressure micro switch (80) and the negative air pressure micro switch (90) and return to the homing sensor (70) so as to provide proper positive air pressure and negative air pressure for visual care.

Figure 6:
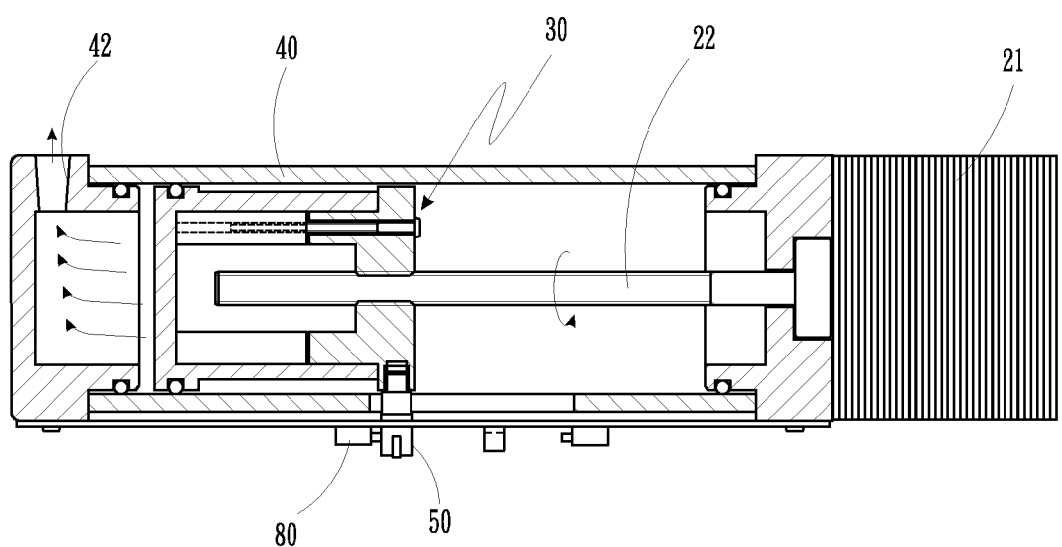
FIG. 6 is a schematic view to show operation of positive air pressure.

FIG. 6 is a schematic view to show operation of positive air pressure. The motor (21) drives the power screw (22) to turn clockwise, and the piston unit (30) is driven to move toward the outlet (42) of the pneumatic cylinder (40) and sends the air to the eyeshade. The eyeshade will generate positive air pressure for visual care. The guide member (50) is moved along with the piston unit (30) to touch the positive air pressure micro switch (80) and to stop the motor (21) from pressurizing continually.

Figure 7:
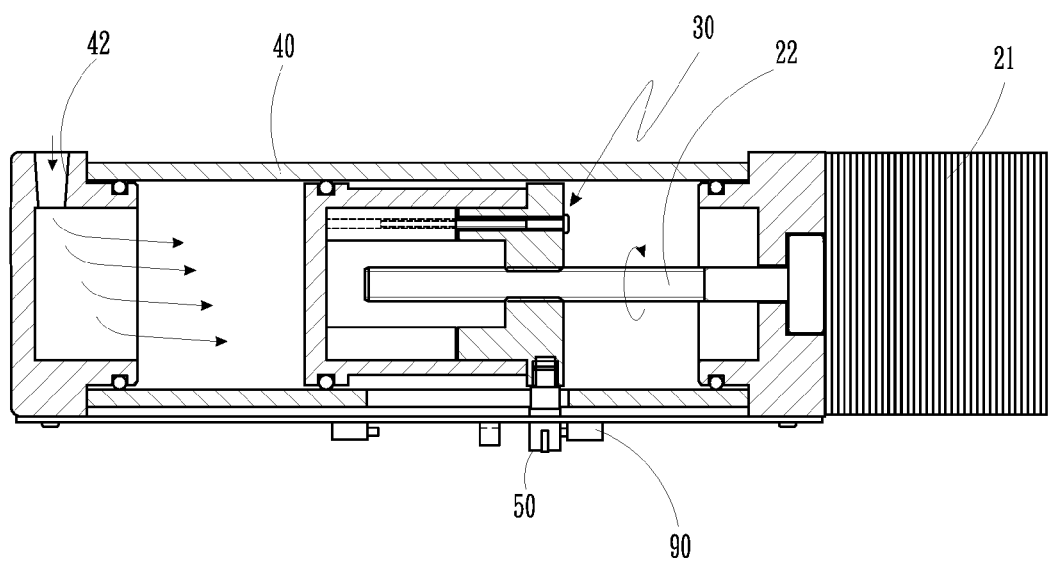
FIG. 7 is a schematic view to show operation of negative air pressure.

FIG. 7 is a schematic view to show operation of negative air pressure. The motor (21) drives the power screw (22) to turn counterclockwise, and the piston unit (30) is driven to be away from the outlet (42) of the pneumatic cylinder (40) and draws the air from the eyeshade. The eyeshade will generate negative air pressure for visual care. The guide member (50) is moved along with the piston unit (30) to touch the negative air pressure micro switch (90) and to stop the motor (21) from pressurizing continually.

The advantages of the present invention are listed below:

1. Proving an innovative configuration. The power unit is activated to turn the power screw and the power screw drives the piston unit to bring the inductive part of the guide member to the homing sensor for return-to-zero setting and to bring the guide member to touch the positive air pressure micro switch and the negative air pressure micro switch and return to the homing sensor to provide proper positive air pressure and negative air pressure for visual care.

2. Providing a specific design. The circuit control panel comprises the homing sensor, the positive air pressure micro switch and the negative air pressure micro switch. The guide member comprises the inductive part which has a bent section facing the homing sensor. Accordingly, the present invention provides a return-to-zero setting to provide proper positive air pressure and negative air pressure for visual care.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A power device for visual care, comprising a power unit, a piston unit, a pneumatic cylinder, a guide member and a circuit control panel, the power unit comprising a motor and a power screw driven by the motor, the piston unit comprising a screw seat and a piston, the screw seat having a threaded hole for insertion of the power screw, the pneumatic cylinder being fitted on the piston and the screw seat of the piston unit, the pneumatic cylinder having a guide slot disposed on one side thereof, the guide member being inserted in the guide slot and fixed to the screw seat, the circuit control panel being fixed to the side having the guide slot of the pneumatic cylinder, the circuit control panel having a notch corresponding in position to the guide slot, the circuit control panel comprising a homing sensor, a positive air pressure micro switch and a negative air pressure micro switch which are located close to the notch and respectively correspond to a homing position, an utmost positive air pressure position and an utmost negative air pressure position of the piston unit, the guide member comprising an inductive part which has a bent section facing the homing sensor, wherein, when the power unit is activated, the power screw drives the piston unit to bring the inductive part of the guide member to the homing sensor for a return-to-zero setting and to bring the guide member to touch the positive air pressure micro switch and the negative air pressure micro switch and return to the homing sensor so as to provide positive air pressure and negative air pressure for visual care.

2. The power device for visual care as claimed in claim 1, wherein the circuit control panel is fixed to the side having the guide slot of the pneumatic cylinder by a plurality of screws which are inserted in holes of the circuit control panel and fixed to threaded holes of the pneumatic cylinder.

* * * * *